United States Patent

Sugimura et al.

[11] Patent Number: 6,059,805
[45] Date of Patent: May 9, 2000

[54] CORNEAL SURGICAL APPARATUS

[75] Inventors: Masahiro Sugimura; Katsuhiko Kozawa; Hirokatsu Makino, all of Aichi, Japan

[73] Assignee: Nidek Co., Ltd., Gamagori-shi, Japan

[21] Appl. No.: 09/281,958

[22] Filed: Mar. 31, 1999

[30] Foreign Application Priority Data

Mar. 31, 1998 [JP] Japan .................. 10-125440
Dec. 9, 1998 [JP] Japan .................. 10-350167

[51] Int. Cl.⁷ .................................................. A61F 9/00

[52] U.S. Cl. ............................................................ 606/166

[58] Field of Search ................................ 606/166, 169, 606/167, 107, 180, 172

[56] References Cited

U.S. PATENT DOCUMENTS 5,964,776  10/1999  Peyman .................................. 606/166
5,972,011  10/1999  Pierce et al. ........................... 606/166

*Primary Examiner*—Michael Buiz
*Assistant Examiner*—Kevin Truong
*Attorney, Agent, or Firm*—Finnegan, Henderson, Farabow, Garrett & Dunner, L.L.P.

[57] ABSTRACT

In a corneal surgical apparatus for incising a cornea of a patient's eye in a layered form, a suction ring is fixedly provided on a main body. The suction ring has an opening from which the cornea of the patient's eye is projected. An applanating portion is provided, which has a flat side abutting against the cornea of the patient eye projected from the opening of the suction ring. A blade is supported movably along said suction ring in a space defined between the suction ring and the flat side of the applanating portion. A projection is associated with the blade to increase the space as the blade incises the cornea.

22 Claims, 9 Drawing Sheets

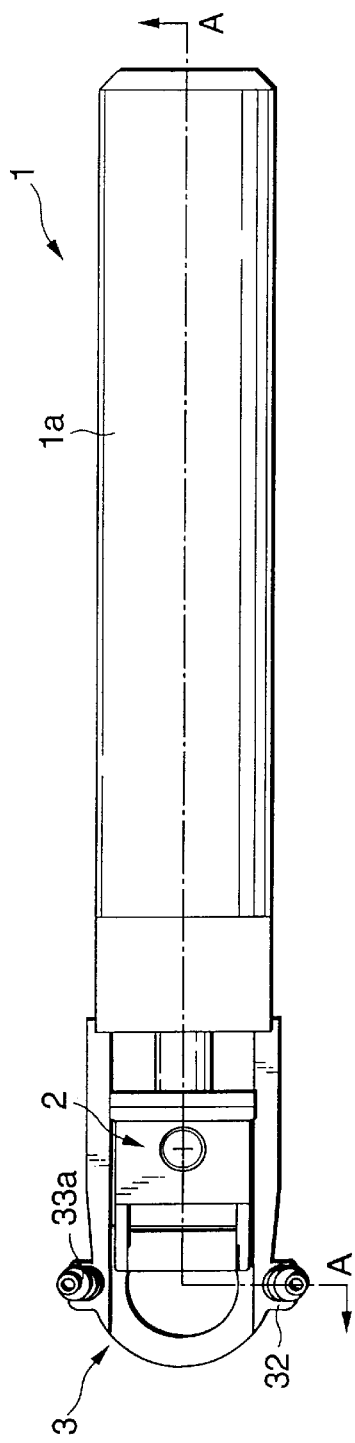
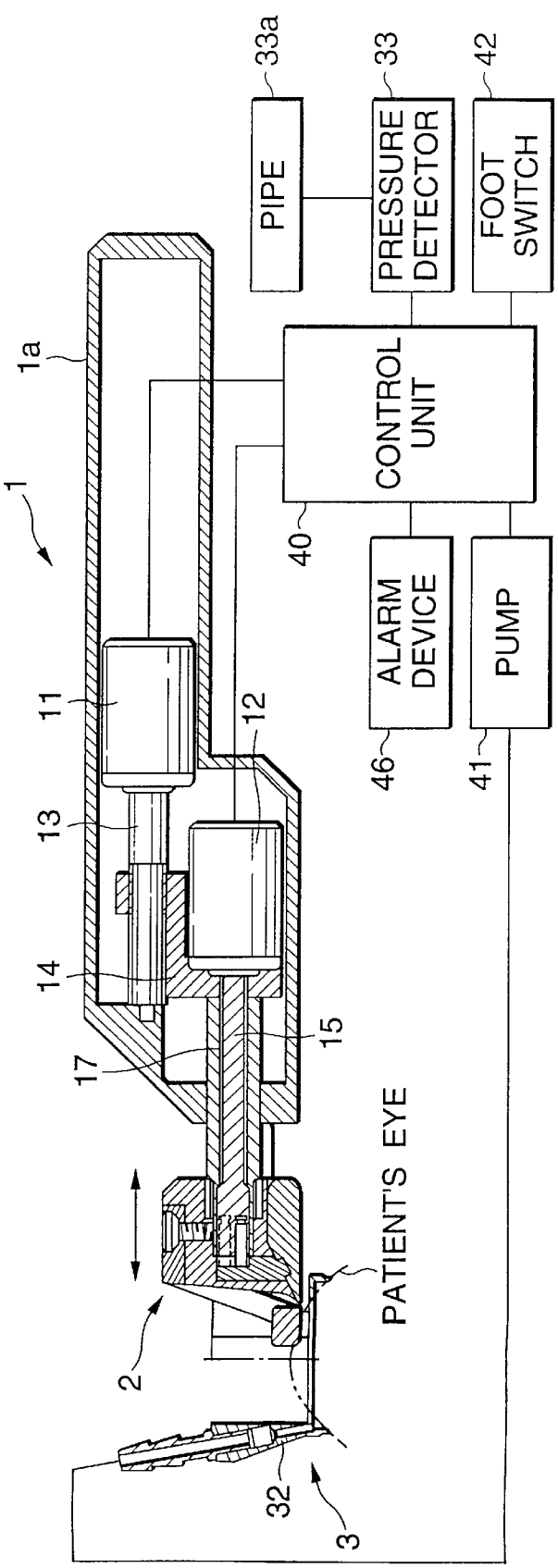
FIG.1A
FIG.1B

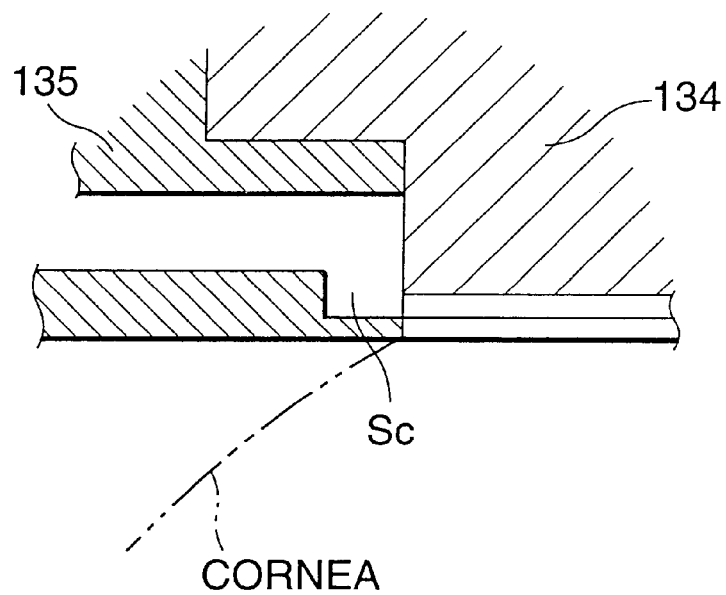

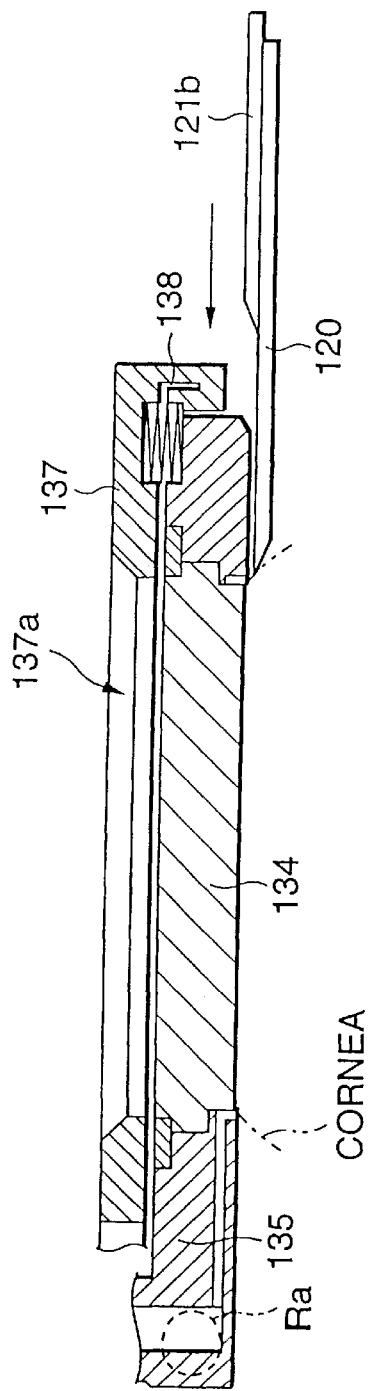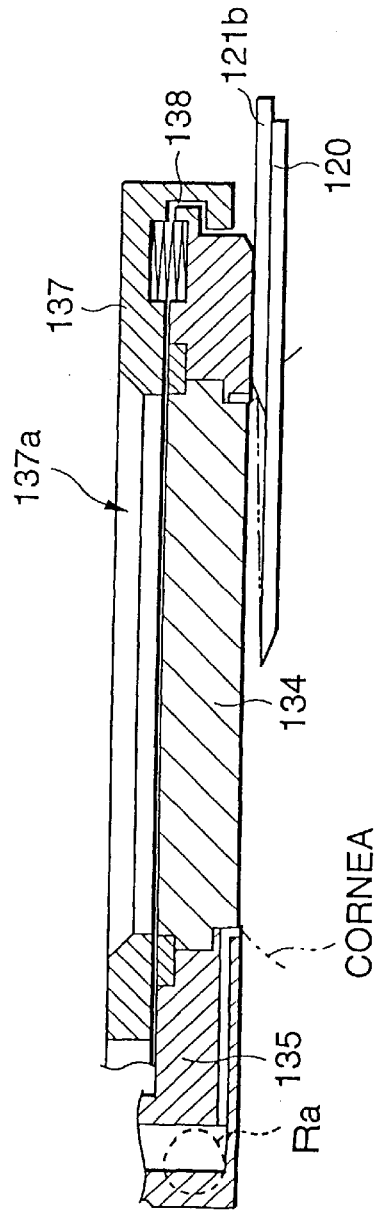

CORNEAL SURGICAL APPARATUS

BACKGROUND OF THE INVENTION

1. Field of the Invention

The present invention relates to a corneal surgical apparatus for incising the cornea of an eye of a patient in a layered form at the time of a keratorefractive surgery or the like.

2. Description of the Related Art

In recent years, attention has been focused on LASIK (laser in situ keratomileusis) surgery for effecting keratorefractive treatment wherein after a flap is formed by incising a corneal portion with a thickness of 150 μm ranging from the corneal epithelium to the corneal stroma with one end of the cornea remaining connected like a hinge, the corneal stroma is cut away or ablated in a refractive correction amount by excimer laser light, and the flap is then returned to its original position. In this LASIK surgery, a corneal surgical apparatus called a microkeratome is used to incise the cornea in a layered form.

A typical microkeratome includes a suction ring to be vacuum-fixed to a part of the cornea ranging from a corneal ring portion to the surface of the conjunctiva, a cornea applanating member for applanating the cornea flatly, and a blade linearly or rotatively moved in the direction toward the hinge while being oscillated in the lateral direction so as to incise the flattened cornea into a layered form with a substantially uniform thickness. During the corneal incision, the cornea is likely to escape due to the movement of the blade, and therefore a certain degree of corneal rigidity is required. To meet this requirement, some microkeratomes employ such a method that the suction pressure applied to the interior of the suction ring is heightened to increase the intraocular pressure of the patient's eye, thereby obtaining the corneal rigidity.

Another method has been proposed in which the cornea applanating member is designed to have a higher friction coefficient or the cornea applanating member is provided with a suction port to suck the corneal upper surface (i.e. the flap-forming side of the cornea) while applanating the same, thereby increasing the resisting force of the cornea against the advance of the blade.

However, the former method may cause an adverse effect on the optic nerves since this method relies on the high intraocular pressure created by increasing the suction pressure applied to the interior of the suction ring.

Further, if the vacuum-fixation of the suction ring is not sufficient, or a suction tube or the like is clogged with a foreign object, there are cases where the air pressure in the space between the patient's eye and the suction ring fails to be set in a sufficient negative pressure, or the air pressure rises (the pressure tends to rise toward the positive pressure) during the surgery. As a result, a problem arise in that the corneal rigidity of the patient's eye fails to be enhanced sufficiently, which makes the incision impossible, or even if the incision is possible, the cut surface becomes nonuniform.

In contrast, the latter method is advantageous in that the intraocular pressure of the patient's eye need not be increased since the escape of the cornea from the blade can be suppressed even if the suction pressure applied to the suction ring is lowered. This method, however, suffers from another problem in that the flap is cut off in the course of the surgery, or the cut surface becomes nonuniform since the applanation and suction of the corneal upper surface by the cornea applanating member increases the frictional force between the flap and the blade in association with the advance of the blade during incision.

SUMMARY OF THE INVENTION

In view of the above-described problems, it is an object of the present invention to provide a corneal surgical apparatus which is capable of effecting the incision of the cornea easily and satisfactorily.

To overcome the above-described problems, the present invention is characterized by the following features.

(1) A corneal surgical apparatus for incising a cornea of a patient s eye in a layered form, includes:

fixing means adapted to abut against the patient's eye, the fixing means having an opening from which the cornea is projected;

first sucking means for sucking air in a gap formed between the fixing means and the patient's eye, so as to fix the fixing means to the patient's eye;

a blade for incising the cornea projected from the opening;

oscillating means for laterally oscillating the blade;

blade moving means for rectilinearly moving the blade in an incising direction;

applanating means for applanating the cornea, the applanating means including a flat plate defining a flat side opposing the cornea, and second sucking means for sucking air in a gap between the flat plate and the cornea;

plate moving means for moving the flat plate in a direction away from a surface of the blade in conjunction with the rectilinear movement of the blade by the blade moving means;

pressure detecting means for detecting air pressure in the gap which changes due to the suction by the first sucking means; and drive controlling means for controlling at least one of the oscillating means and the blade moving means on the basis of information on the pressure detected by the pressure detecting means.

(2) The corneal surgical apparatus according to (1), wherein the plate moving means includes:

rotating means for rotating the flat plate in a vertical direction about a shaft provided at one end of the fixing means; and a projection provided above the blade to upwardly push the flat plate without interposing the incised cornea between the projection and the flat plate.

(3) The corneal surgical apparatus according to (1), further includes:

suction controlling means for controlling the first sucking means on the basis of the information on the pressure detected by the pressure detecting means.

(4) A corneal surgical apparatus for incising the cornea of a patient's eye in a layered form, includes:

fixing means adapted to abut against the patient's eye, the fixing means having an opening from which the cornea is projected;

sucking means for sucking air in a gap formed between the fixing means and the patient 's eye so as to fix the fixing means to the patient's eye;

a blade for incising the cornea projected from the opening;

driving means for driving the blade;

pressure detecting means for detecting air pressure in the gap which changes due to the suction by the sucking means; and drive controlling means for controlling the driving means on the basis of information on the pressure detected by the pressure detecting means.

(5) The corneal surgical apparatus according to (4), wherein the driving means includes oscillating means for laterally oscillating the blade and moving means for rectilinearly or rotatively moving the blade in an incising direction, and the drive controlling means controls at least one of the oscillating means and the moving means on the basis of the information on the pressure detected by the pressure detecting means.

(6) The corneal surgical apparatus according to (5), wherein the drive controlling means linearly adjusts at least one of the number of oscillations of the oscillating means and a moving velocity of the moving means on the basis of the air pressure detected by the pressure detecting means.

(7) The corneal surgical apparatus according to (5), wherein the drive controlling means determines which one of a plurality of stages the air pressure detected by the pressure detecting means belongs to, and adjusts at least one of the number of oscillations of the oscillating means and a moving velocity of the moving means on the basis of the stage thus determined.

(8) The corneal surgical apparatus according to (4), further includes;

upper-limit setting means for setting a value of an upper limit tor the detected air pressure, wherein the drive controlling means stops the operation of the driving means when the value of the air pressure detected by the pressure detecting means is more positive than the value of the upper limit.

(9) The corneal surgical apparatus according to (8), further includes:

alarm means for notifying an operator of a fact that the value of the air pressure detected by the pressure detecting means is more negative than the value of the upper limit.

(10) The corneal surgical apparatus according to (4), further includes:

lower-limit setting means for setting a value of a lower limit for the detected air pressure, wherein the drive controlling means stops the operation of the driving means when the value of the air pressure detected by the pressure detecting means is more negative than the value of the lower limit.

(11) The corneal surgical apparatus according to (8), further includes:

lower-limit setting means for setting a value of a lower limit for the detected air pressure, wherein the drive controlling means stops the operation of the driving means when the value of the air pressure detected by the pressure detecting means is more negative than the value of the upper limit.

(12) The corneal surgical apparatus according to (4), further includes;

upper-limit setting means for setting a value of an upper limit for the detected air pressure, wherein the drive controlling means starts the operation of the driving means when the value of the air pressure detected by the pressure detecting means is more negative than the value of the upper limit.

(13) The corneal surgical apparatus according to (4), further includes:

suction controlling means for controlling the sucking means on the basis of the information on the pressure detected by the pressure detecting means.

(14) The corneal surgical apparatus according to (5), wherein the moving means includes means for rectilinearly moving the blade, and the apparatus further comprising:

applanating means for applanating the cornea, the applanating means including a flat plate defining a flat side opposing the cornea and second sucking means for sucking air in a gap between the flat plate and the cornea; and second moving means for moving the flat plate in a direction away from a surface of the blade in conjunction with the rectilinear movement of the blade by the moving means.

(15) The corneal surgical apparatus according to (14), wherein the second moving means includes;

rotating means for rotating the flat plate in a vertical direction about a shaft provided at one end of the fixing means; and a projection provided above the blade to upwardly push the flat plate without interposing the incised cornea between the projection and the flat plate.

(16) A corneal surgical apparatus for incising the cornea of a patient's eye in a layered form, includes:

fixing means adapted to abut against the patient's eye, the fixing means having an opening from which the cornea is projected;

a blade for incising the cornea projected from the opening;

blade moving means for rectilinearly moving the blade in an incising direction;

applanating means for applanating the cornea, the applanating means including a flat plate defining a flat side opposing the cornea and second sucking means for sucking air in a gap between the flat plate and the cornea; and plate moving means for moving the flat plate in a direction away from a surface of the blade in conjunction with the rectilinear movement of the blade by the blade moving means.

(17) The corneal surgical apparatus according to (16), wherein the plate moving means has rotating means for rotating the flat plate in a vertical direction about a shaft provided at one end of the fixing means.

(18) The corneal surgical apparatus according to (16), wherein the plate moving means includes:

rotating means for rotating the flat plate in a vertical direction about a shaft provided at one end of the fixing means; and a projection provided above the blade to upwardly push the flat plate without interposing the incised cornea between the projection and the flat plate.

(19) The corneal surgical apparatus according to (16), wherein the blade has frictional-force reducing means for reducing a frictional force acting on the cornea cut in the layered form.

(20) The corneal surgical apparatus according to (19), wherein the frictional-force reducing means includes a frictional-force reducing coating applied on a surface of the blade which comes into contact with the cornea cut in the layered form.

(21) The corneal surgical apparatus according to (16), further includes:

urging means for urging the flat plate toward a surface of the blade.

(22). The corneal surgical apparatus according to (16), further includes:
oscillating means for laterally oscillating the blade.

(23) A corneal surgical apparatus for incising a cornea of a patient's eye in a layered form, includes:
a main body;
a suction ring fixedly provided on the main body, the suction ring having an opening from which the cornea of the patient's eye is projected;
an applanating portion having a flat side abutting against the cornea of the patient eye projected from the opening of the suction ring;
a blade movable along the suction ring in a first space defined between the suction ring and the flat side of the applanating portion;
a first suction passage communicated with the first space; and
a projection associated with the blade to increase the first space as the blade incises the cornea.

(24) The corneal surgical apparatus according to (23), further includes:
a second suction passage communicated with a second space that is defined between the suction ring and the cornea and that is located opposite from the first space with respect to the blade;
at least one of pressure detectors which detect air pressure in the first and second spaces, respectively; and
a control unit which controls movement of the blade based on the air pressure detected by the at least one pressure detector.

(25) The corneal surgical apparatus according to (24), wherein the blade is movable rectilinearly in a first direction and oscilatable in a second direction perpendicular to the first direction.

(26) A corneal surgical apparatus for incising a cornea of a patient's eye in a layered form, includes:
a main body;
a suction ring fixedly provided on the main body, the suction ring having an opening from which the cornea of the patient's eye is projected;
a suction passage connected to the suction ring and communicated with a space defined between the suction ring and the cornea;
a blade movable along the suction ring;
a pressure detector which detects air pressure in the space; and
a control unit which controls movement of the blade based on the air pressure detected by the pressure detector.

The present disclosure relates to the subject matter contained in Japanese patent application Nos. Hei. 10-125440 (filed on Mar. 31, 1998) and Hei. 10-350167 (filed on Dec. 9, 1998), which are expressly incorporated herein by reference in their entireties.

BRIEF DESCRIPTION OF THE DRAWINGS

In the accompanying drawings:
FIG. 1A is a plan view of a corneal surgical apparatus in accordance with a first embodiment of the present invention;
FIG. 1B is a cross-sectional view taken along line A—A of FIG. 1A, illustrating a schematic diagram of a control system;
FIG. 7 is an enlarged explanatory diagram of a cornea sucking portion of the apparatus in accordance with the second embodiment;
FIGS. 8A and 8B are explanatory diagrams concerning the incision of the cornea by the apparatus in accordance with the second embodiment.

DESCRIPTION OF THE PREFERRED EMBODIMENT

First Embodiment

Figure 2A:
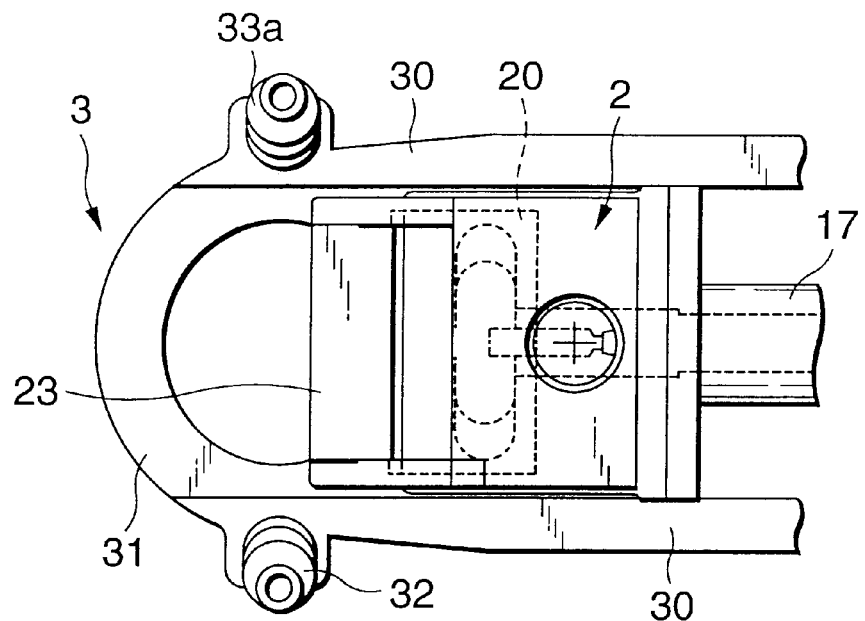
FIGS. 2A and 2B are enlarged explanatory diagrams of a cutting unit and a suction unit of the apparatus in accordance with the first embodiment.

Referring to the accompanying drawings, a description will be given of a first embodiment of the present invention. FIG. 1A is a top view of a corneal surgery apparatus body in accordance with the first embodiment of the present invention, and FIG. 1B is a cross-sectional view taken along line A—A in FIG. 1A and illustrates the schematic configuration of a control system.

Reference numeral 1 denotes a main body of the microkeratome, and numeral 1a denotes a grip portion which is to be held by an operator during a surgery. A suction unit 3 for fixing the apparatus to the patient's eye and a cutting unit 2, which has a blade 20 (which will be described later) for incising the cornea and is adapted to move rectilinearly on the suction unit 3, are provided on the front side (left-hand side in the drawing) of the main body 1.

A feed motor 11 for rectilinearly moving the cutting unit 2 in the incising direction and an oscillating motor 12 for imparting lateral oscillations to the blade 20 are fixedly provided in the main body 1. A feed screw 13 is coupled to a rotating shaft of the motor 11, which has a threaded portion corresponding in length to the rectilinear movement or travel of the cutting unit 2. An attaching member 14 is threadedly engaged with the screw 13. The motor 12 as well as a connecting member 17 for connecting the motor 12 and the cutting unit 2 are fixed to the attaching member 14. As the motor 11 is rotated forwardly or reversely, the motor 12 and the connecting member 17 move forwardly or backwardly through the screw 13 and the attaching member 14, thereby causing the cutting unit 2 to move forwardly or backwardly. Further, a rotating shaft 15 is rotatably held by the connecting member 17. An eccentric shaft 16 is embedded on a distal end of the rotating shaft 15 at a position offset from the center of rotation, and the eccentric shaft 16 imparts lateral oscillations to the blade 20 (which will be described later).

Figure 2B:
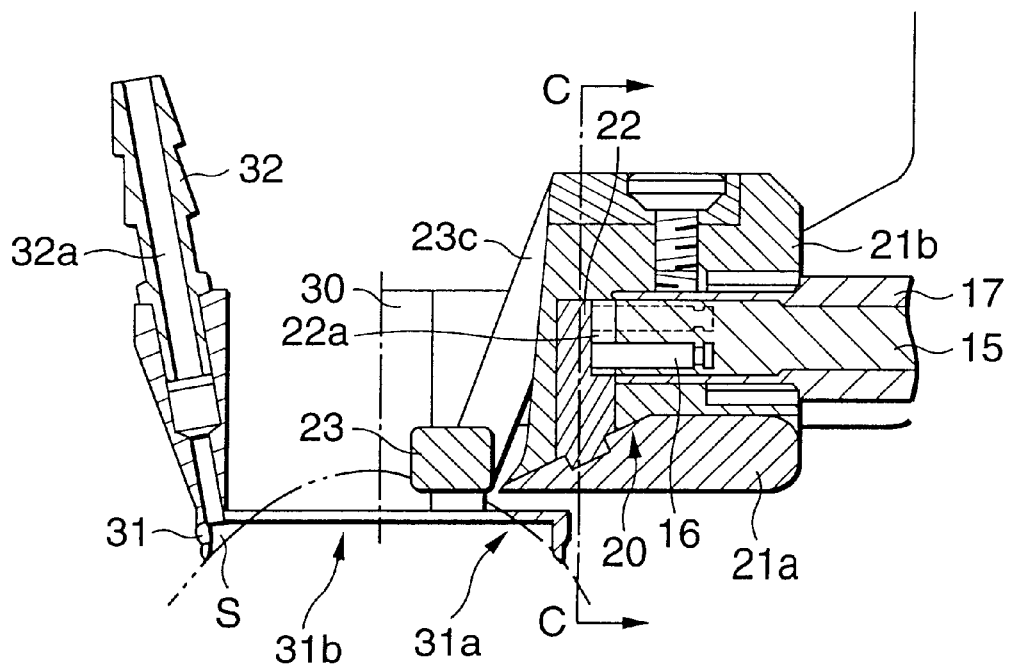
Figure 3:
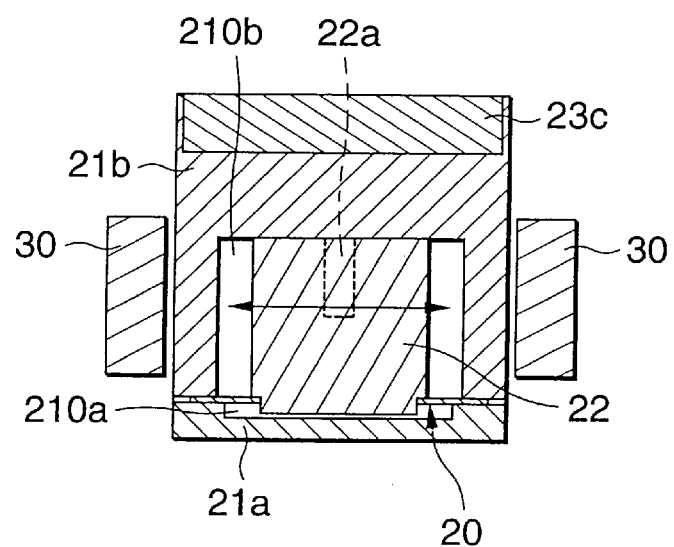
FIG. 3 is a cross-sectional view, taken along line C—C of FIG. 2B, illustrating the cutting unit of the apparatus in accordance with the first embodiment.

Referring next to FIGS. 2A, 2B and 3, a description will be given of the arrangements of the cutting unit 2 and the suction unit 3. FIGS. 2A and 2B are enlarged views of the cutting unit 2 and the suction unit 3 shown in FIGS. 1A and 1B. FIG. 3 is cross-sectional view taken along line C—C of FIG. 2B.

The cutting unit 2 is comprised of the blade 20 for corneal incision; a blade holder 21a and a holder block 21b for holding the blade 20 in such a manner as to permit lateral oscillations; an oscillation transmitting member 22 for transmitting the lateral oscillations generated by the eccentric shaft 16 to the blade 20; and a cornea applanating portion 23 fixed to the block 21b by means of an attaching member 23c. A rotation hole into which the rotating shaft 15 is inserted is provided inside the block 21b, and a tip portion of the connecting member 17 is fixed thereto.

A metal blade having a blade edge of stainless steel, steel, or the like is used as the blade 20, and the blade 20 is held between the holder 21a and the block 21b at an appropriate angle with respect to the horizontal plane in such a manner as to be capable of undergoing lateral oscillations. On the holder 21a side, a shallow recess 210a is formed at a portion where the blade 20 is placed, and the lateral width of the recess 210a is set to be larger than the oscillating width for the lateral oscillations of the blade 20.

The transmitting member 22 is secured to the blade 20, and is movable in the lateral direction within a receiving groove 210b formed in the block 21b. A vertical groove 22a for engagement with the eccentric shaft 16 is formed in the transmitting member 22. When the rotating shaft 15 is rotated by the rotative driving of the motor 12, the eccentric shaft 16 attached to the tip of the rotating shaft 15 and engaged with the vertical groove 22a applies a lateral driving force to the transmitting member 22. This causes the blade 20 to oscillate laterally together with the transmitting member 22.

The applanating portion 23 is provided on the front side (left-hand side in the drawing) of the blade 20 so as to flatly applanate the cornea of the patient's eye in advance of the corneal incision by the blade 20 as the cutting unit 2 is moved forwardly. Since the blade 20 incises the cornea thus applanated flatly by the applanating portion 23, a flap of a uniform layer is formed.

In this embodiment, the distance between the edge of the blade 20 attached to the holder $^2$1a and the lower surface of the applanating portion 23 is set to be about 150 microns ($\mu$m) so that the corneal epithelium can be incised with this thickness in a layered form.

The suction unit 3 includes a fixing member 30, a suction ring 31, and a suction pipe 32. The suction ring 31 is fixed to the main body 1 by the fixing member 30. The suction ring 31 has a substantially hollow cylindrical shape (a substantially U-shape in section), which has a circular recessed portion 31a adapted to abut against the patient's eye, and an opening 31b concentric to the recessed portion 31a. When the suction ring 31 is mounted on the patient's eye in place for surgery, the cornea of the patient's eye projects upward from the opening 31b, and a lower end portion of the suction ring 31 and an opening end portion (a periphery) of the opening 31b are caused to abut against the patient's eye to define a space S for suction.

The suction pipe 32 is embedded in the suction ring 31, and connected through an unillustrated vacuum tube to a pump 41. A suction passage 32a provided inside the suction pipe 32 communicates with the recessed portion 31a, and as the air inside the space S is sucked and discharged by the pump 41 through the passage 32a, the suction ring 31 is vacuum-fixed to the patient's eye. In this fixation, as the operator holds the grip portion 1a of the main body 1, the positioning of the opening 31b can be facilitated, and the apparatus can be hold stably.

In addition, a pipe 33a for pressure detection is embedded in the suction ring 31, and the pipe 33a is connected to a pressure detector 33 through an unillustrated tube. The detector 33 detects the air pressure inside the space S sucked by the pump 41. A control unit 40 controls the operation of the apparatus on the basis of the air pressure detected by the detector 33. If the air pressure within the space S is not set to be a sufficiently negative pressure due to the presence of a gap between the suction ring 31 and the patient's eye or due to the clogging of the passage 32a or the like with a foreign object, there is a possibility that the corneal rigidity is not secured appropriately. For this reason, a predetermined value is preset as an upper limit of the air pressure required to secure the corneal rigidity to a certain extent, and if the detected air pressure is more positive than this predetermined value of the upper limit, the operation of the apparatus (the feeding or oscillation of the blade 20) is stopped (the starting of the apparatus is inhibited if it is detected before the surgery, and the operation of the apparatus is stopped if it is detected during the surgery). In this case, the operator stops the input of a drive instruction signal by a foot switch 42, and checks the state of abutment of the suction ring 31, the state of clogging of the passage 32a, and the like. When the detected air pressure reaches a level more negative than the predetermined pressure of the upper limit, and the operator reinputs the drive instruction signal by the foot switch 42, the apparatus is able to start or resume the operation. For convenience, an alarm device 46 may be used to visually or audibly notify the operator of the fact that the detected air pressure has reached a level more negative than the predetermined value of the upper limit. For example, a buzzer may be provided to continuously generate a sound if the detected air pressure is at a level more positive than the predetermined value of the upper limit, and stop the generation of the sound if the detected air pressure reaches a level more negative than the predetermined value of the upper limit (to the contrary, the buzzer may be designed to generate a sounded for a fixed time period from a time point at which the negative pressure has been reached). Furthermore, the apparatus may be designed such that it become operable to start the incision after the detected air pressure has reached a level more negative than the predetermined value of the upper limit.

On the other hand, the excessively negative air pressure within the space S caused due to an excessively long suction time or the like is not preferable since the intraocular pressure of the patient's eye becomes too high. For this reason, a predetermined value is preset as a lower limit of the air pressure to avoid such a situation. That is, the operation of the apparatus is stopped if the detected air pressure has reached a level more negative than the predetermined value of this lower limit. This makes it possible to perform the surgery without imposing the adverse effect on the patient's eye.

Figure 4A:
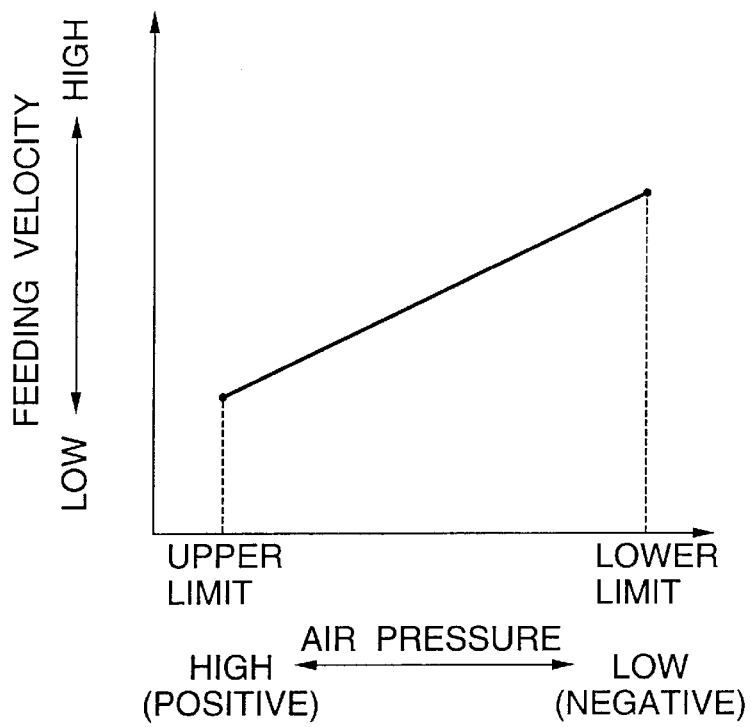
FIGS. 4A and 4B are explanatory diagrams concerning control of the feeding velocity of a blade with respect to detected air pressure.
Figure 4B:
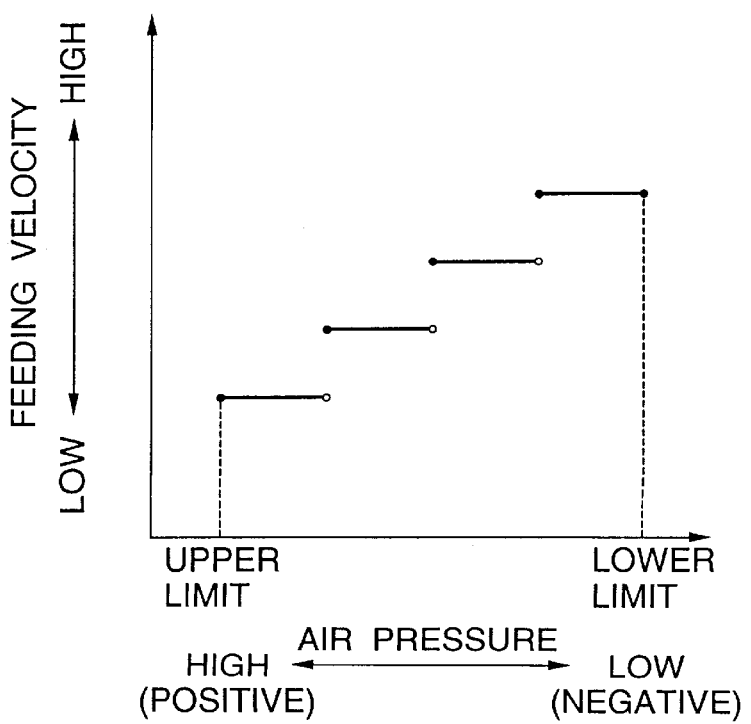

Although the blade is driven with a predetermined feeding velocity and a predetermined number of oscillations basically, these conditions may be changed depending on the detected air pressure. For example, as for the feeding velocity, if the air pressure has dropped (toward the negative pressure) to increase the corneal rigidity, the feeding velocity may be made high, whereas if the air pressure has risen (toward the positive pressure) to decrease the corneal rigidity, the feeding velocity may be made slow. Such change may be effected linearly as shown in FIG. 4A, or in stepwise manner as shown in FIG. 4B. This modification makes the surgery more efficient and accurate.

In addition, the predetermined values of the upper and lower limits for the air pressure as described above may be preset as fixed values, or may be variably set by the operator using an unillustrated switch or the like.

The control unit 40 is connected to the detector 33, the foot switch 42, and the like. The control unit 40 controls the operation of the motors 11 and 12 and the pump 41.

Hereafter, a description will be given of the operation of the apparatus having the above-described configuration While confirming the state of inclination of the suction ring 31 (main body 1), the position of the pupillary center, and the like on the basis of a mark that has boon preliminarily applied on the patient's cornea using an instrument ouch as a marker, the operator aligns the center of the opening 31b with the pupillary center, and disposes the suction ring 31 on the patient's eye.

After installation of the suction ring 31, the operator, while keeping the position and the posture of the main body 1, operates the pump 41 to suck the air in the space S between the suction ring 31 and the patient's eye to thereby decrease the air pressure (toward the negative pressure). When the air pressure in the space S is decreased to a fixed value (when it reaches a sufficient negative pressure), the operation of the pump 41 is controlled by a control unit 40 so as to maintain that air pressure and vacuum-fix the suction ring 31 onto the patient's eye.

After completion of the fixation of the apparatus, the operator operates the foot switch 42 to rotatively drive the motor 11 and the motor 12. As described above, the control unit 40 controls the driving of the motors 11 and 12 or the appratus on the basis of the air pressure detected by the detector 33. Since the blade 20 undergoes one oscillation per one revolution of the rotating shaft 15, the number of oscillations of the blade 20 per unit time can be controlled easily by changing the number of revolutions of the motor 12 per unit time. The rotative drive of the motor 11 causes the cutting unit 2 to move rectilinearly toward the hinge with the aid of the attaching member 14 and the connecting member 17. Concurrently, the rotating shaft 15 slides in the advancing direction integrally with the cutting unit 2 while making rotational motion for imparting lateral oscillations to the blade 20.

Under the independent control of the motors 11 and 12 as described above, the blade 20 gradually incises the cornea of the patient's eye consecutively applanated flatly by the applanating portion 23. The surgery proceeds in this manner.

When the flap formation is complete, that is, the edge or the blade 20 has incised the cornea with the hinge portion left, the motor 11 is rotated reversely to return the cutting unit 2 to its initial position. For this return operation, the rotation of the motor 12 is only stopped using the independent control of the motors 11 and 12, to thereby withdraw or remove the blade 20 from the flap while avoiding the unnecessary oscillation of the blade 20. This reduces the possibility that the flap thus formed is cut off during the course of the return operation.

Figure 5A:
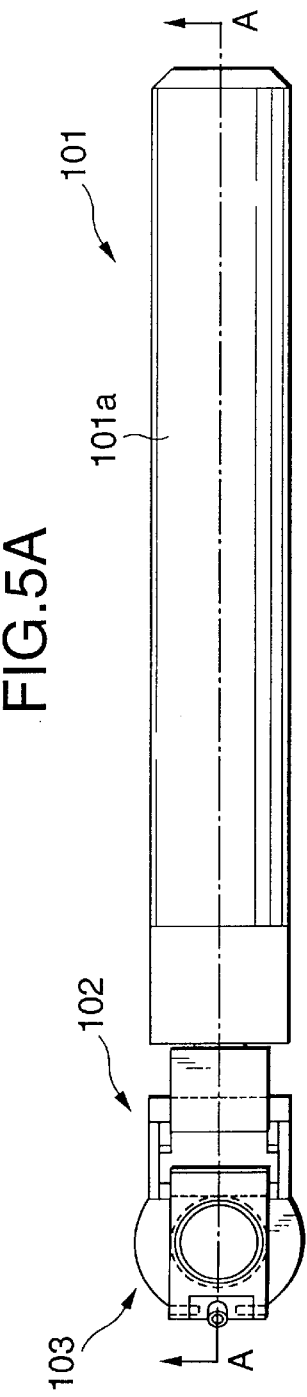
FIG. 5A is a plan view of a corneal surgical apparatus in accordance with a second embodiment of the present invention.
Figure 5B:
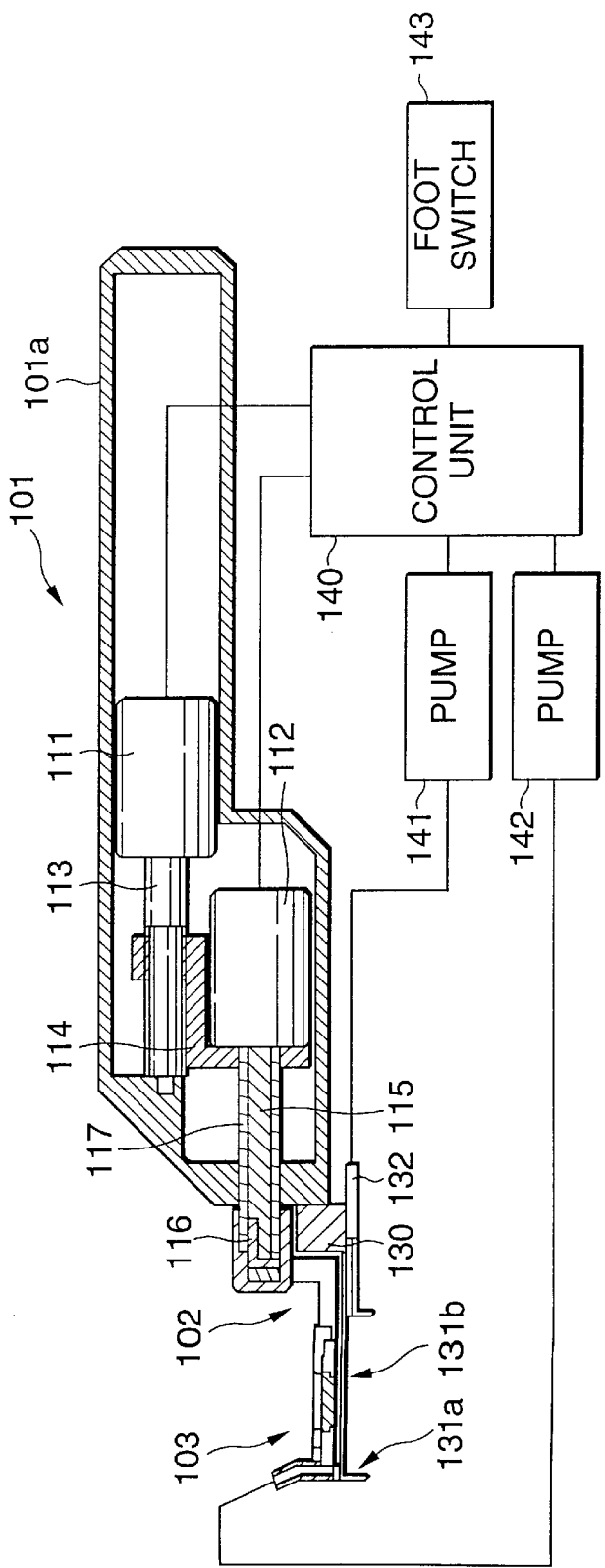
FIG. 5B is a cross-sectional view taken along line A—A or FIG. 5A, and also illustrates a schematic diagram of a control system.

After the cutting unit 2 is returned to its initial position, the air is introduced into the space S to release the suction, and the apparatus is removed. Subsequently, a refractive correction amount of the corneal stroma is ablated and removed using laser light, and then the flap is returned to its original position, thereby completing the surgery, Second Embodiment Referring now to FIGS. 5A to 9, a description will be given of another embodiment of the present invention. FIG. 5A is a top view of a corneal surgery apparatus body in accordance with a second embodiment of the present invention, and FIG. 5B is a cross-sectional view taken along line A—A in FIG. 5A and illustrates the schematic configuration of a control system.

Reference numeral 101 denotes a main body of the microkeratome, and numeral 101a denotes a grip portion which is to be held by the operator during a surgery. A cutting unit 102 and a suction unit 103 are provided on the front side (left-hand side in the drawing) of the main body 101.

A feed motor 111 for rectilinearly moving a cutting blade 120 (which will be described later) of the cutting unit 102 in the incising direction and an oscillating motor 112 for imparting lateral oscillations to the blade 120 are provided in the main body 101. A feed screw 113 is coupled to a rotating shaft of the motor 111. The length of a threaded portion of the feed screw 113 corresponds to the rectilinear movement amount of the cutting unit 102. An attaching member 114 is threadedly engaged with the screw 113, and a tubular connecting member 117 for connecting the motor 112 and the cutting unit 102 as well as the motor 112 are fixed to the attaching member 114. As the motor 111 is rotated forwardly or reversely, the motor 112 and the connecting member 117 move forwardly or backwardly through the screw 113 and the attaching member 114, thereby causing the cutting unit 102 to move forwardly or backwardly. Further, a rotating shaft 115 connected to a rotating shaft of the motor 112 is rotatably held by the connecting member 117. An eccentric shaft 116 is embedded on a distal end of the rotating shaft 115 and disposed at a position offset from the center of rotation of the shaft 115.

Figure 6A:
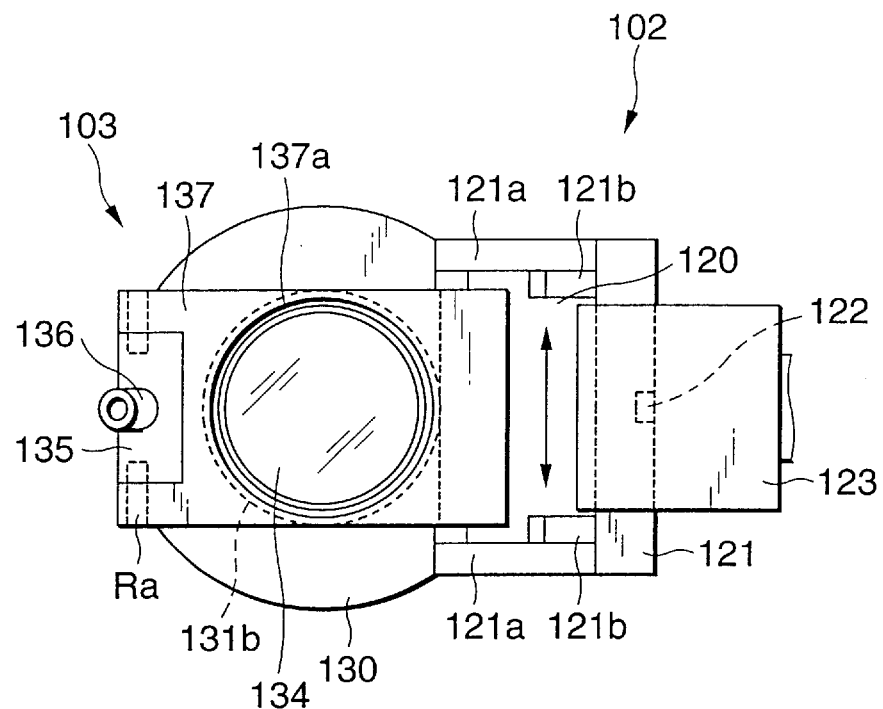
FIGS. 6A and 6B are enlarged explanatory diagrams of a cutting unit and a suction unit of the apparatus in accordance with the second embodiment.
Figure 6B:
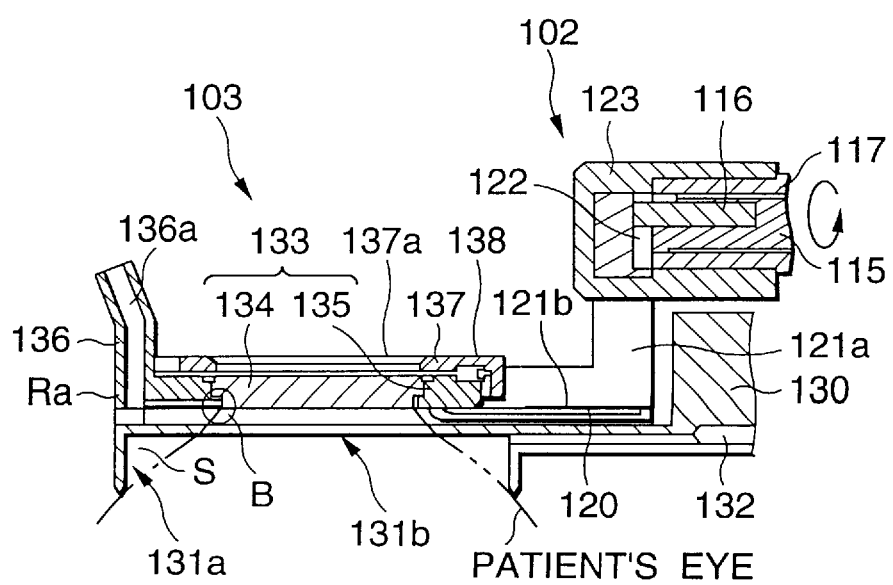

Referring next to FIGS. 6A and 6B, a description will be given of the arrangements of the cutting unit 102 and the suction unit 103. FIGS. 6A and 6B are enlarged views of the cutting unit 102 and the suction unit 103 shown in FIGS. 5A and 5B.

The cutting unit 102 includes the blade 120 for incising the cornea; a blade holder 121 having two L-shaped arms 121a for supporting the blade 120 at its lower end; and a holding member 123 attached to the distal end of the connecting member 117 to suspend and hold the holder 121 in such a manner as to permit the lateral movement thereof. A vertical groove 122 for receiving and engaging the eccentric shaft 116 is formed in the holder 121 held by the holding member 123. When the rotating shaft 115 is rotated by the rotative driving of the motor 112, the eccentric shaft 116, provided on the distal end of the shaft 115 and engaged with the vertical groove 122, applies a lateral driving force to the holder 121, so that the blade 120 oscillates laterally together with the holder 121.

The blade 120 is a metal blade having a blade edge of stainless steel, steel, or the like, and a fluororesin coating for reducing the friction is applied to an upper surface of the blade with which the flap comes into contact during the course of the flap formation. A pair of projections 121b, each having an inclined surface at its distal end portion in the advancing direction, are located at respective sides of the blade 120 on the upper rear surface of the blade 120. As the holder 121 is advanced to proceed with the corneal incision by the blade 120, the projections 121b enter below a cornea applanating portion 133 (which will be described later) to push the applanating portion 133 upward. The width of each projection 121b is set to such a size as not to deviate from the laterally oscillating applanating portion 133, and the interval or distance between the two projections 121b is set to such a length as to permit the incised cornea flap to pass therebetween. In order to reduce the contact between the upper surface of the blade 120 and the incised cornea flap, the height of each projection 121b is set to such a height that an end portion of the cornea flap rise about 10 microns ($\mu$m) from its initial applanated position upon completion of the incision with the hinge left. These projections 121b may be formed on the inner sides of the two arms 121a, respectively.

In this case, if recesses or relief portions, which avoids the interfere of the blade 120 with the projections 121*b*, are provided on the blade 120 side, the projections 121*b* can have a sufficient thickness.

The suction unit 103 is fixed to the main body 101 through a suction base 130. The base 130 includes a circular recessed portion 131*a* for abutment against the corneal ring portion of the patient's eye, and an opening 131*b* concentric to the recessed portion 131*a*. The recessed portion 131*a* is connected to an unillustrated vacuum tube through a suction passage 132 formed in the base 130 to be communicated with a pump 141. For the surgery, an end portion of the recessed portion 131*a* and an opening end of the opening 131*b* are made to abut against a portion of the cornea of the patient's eye ranging from the corneal ring portion to the conjunctiva, and then the air in the space S secured by this abutment is sucked, thereby vacuum-fixing the base 130 onto the cornea to the extent that the intraocular pressure of the patient's eye will not be heightened excessively. In this fixation, the operator can hold the grip portion 101*a* of the main body 101 to facilitate the positioning of the opening 131*b* and make the entire apparatus stable.

The applanating portion 133 and a connecting end 136 for connection to the suction tube (not shown) are supported on top of the base 130 so as to be pivotable about a supporting shaft (axis) Ra. The applanating portion 133 includes a transparent portion 134 in its central region, which is formed of a material such as polymethyl methacrylate (PMMA), and a peripheral portion 135 surrounding the transparent portion 134. As shown in FIG. 7 (which is an enlarged view of a "B" portion in FIG. 6B), an annular or circular gap Sc is formed in a lower portion of the peripheral portion 135 along the boundary between the transparent portion 134 and the peripheral portion 135 so as to laterally sucking the corneal surface deformed by being pressed by the transparent portion 134. The gap Sc is communicated with a suction passage 136*a* formed through the connecting end 136. When the base 130 is placed in abutment against the corneal ring portion of the patient's eye, the gap Sc circumscribes and abuts against the peripheral portion of the corneal surface. As the suction pressure is applied by a pump 142 connected to the suction passage 136*a* under this condition, the applanating portion 133 is secured to the cornea of the patient's eye. Since the corneal surface is sucked through the gap Sc laterally, the deformation associated with the suction during the incision by the blade 120 can be limited to the periphery of the flap where an optical effect is small.

The interval or distance between the upper surface of the blade 120 attached to the holder 121 and the transparent portion 134 is set to be about 150 microns ($\mu$m) so that the corneal epithelium is incised with this thickness in a layered form.

An outer covering portion 137 secured to an upper front end (left-hand side in FIG. 6B) of the base 130 is disposed on the applanating portion 133, and the outer covering portion 137 restricts the rotation or pivotal motion of the applanating portion 133 in the vertical direction. The outer covering portion 137 is provided with an opening 137*a* which is concentric to the opening 131*b* and the transparent portion 134. The operator can observe the cornea being incised through this opening 137*a*, the transparent portion 134, and the opening 131*b*. A resilient member 138 such as a spring is interposed between the outer covering portion 137 and the applanating portion 133 to apply a downwardly depressing force to the applanating portion 133.

In FIG. 5B, reference numeral 140 denotes a control unit of the corneal surgical apparatus, which is connected to a foot switch 143 to control the operation of the motors 111 and 112 and the pumps 141 and 142.

Hereafter, a description will be given of the operation of the apparatus having the above-described configuration. While confirming the state of inclination of the suction unit 103 (main body 101), the position of the pupillary center, and the like on the basis of a mark preliminarily applied onto the patient's cornea using an instrument such as a marker, the operator aligns the center of the opening 137*a* with the pupillary center, and disposes the base 130 on the cornea of the patient's eye (a position mark may be provided on the transparent portion 134 which can be observed through the opening 137*a*).

After installation of the suction unit 103, the operator, while keeping the position and the posture of the main body 101, operates the pump 141 to suck the air in the space S between the base 130 and the corneal surface, thereby decreasing the air pressure. When the air pressure in the space S is decreased to a fixed value, the operation of the pump 141 is controlled by the control unit 140 so as to maintain that air pressure and vacuum-fix the base 130 onto the patient's eye. As for the suction pressure, since it suffices if the suction base 130 is fixed to such an extent that it does not move during the surgery in the state in which the suction unit 103 and the main body 101 are being held by the operator, the intraocular pressure of the patient's eye is prevented from rising to a high level.

The vacuum-fixation of the suction unit 103 causes the applanating portion 133 to flatly applanate the cornea of the patient's eye. Subsequently, the pump 142 is driven to reduce the air pressure within the gap Sc in abutment with the cornea, thereby vacuum-fixing the upper surface of the cornea in a state where it is pressed by the applanating portion 133.

After completion of the fixation of the apparatus, the operator operates the foot switch 143 to rotatively drive the motor 111 and the motor 112. The blade 120 incises the cornea while being oscillated laterally by the motor 112 and being moved by the motor 111 rectilinearly in the direction to form the hinge, thereby performing corneal incision to form the flap.

Referring to FIGS. 8A and 8B, a description will be given of this corneal incision in more detail. FIG. 8A shows a state in which the corneal incision is to be started. Since the upper surface of the cornea is sucked by the applanating portion 133, even if the suction pressure on the base 130 side is not so high, it is possible to obtain sufficient corneal rigidity to bear against the advance of the blade 120 and make the smooth incision possible.

FIG. 8B shows a state in which the incision has progressed midway. As the corneal incision progresses, that is, the blade 120 gradually advances toward the hinge, the projections 121*b* provided on the blade 120 enter below the lower end of the applanating portion 133 to gradually push the applanating portion 133 (to gradually rotate the applanating portion 133 about the supporting shaft (axis) Ra) upwardly against a downward pressing force exerted on the applanating portion 133 by the resilient member 138. Since the flap portion formed by the incision is being sucked onto the applanating portion 133 side through the gap Sc, the flap portion is pushed upward together with the applanating portion 133. Consequently, the contact portion of the incised flap with the blade 120 is reduced (a gap is secured between the flap and the blade 120) to reduce the frictional force acting therebetween. Accordingly, it is possible to protect the flap from being cut off due to the effect of the frictional force, and to obtain the satisfactory cut surface. Further, since the incision by the blade 120 proceeds while the incised portion of the cornea is being enlarged, the flap can be formed smoothly.

Figure 9:
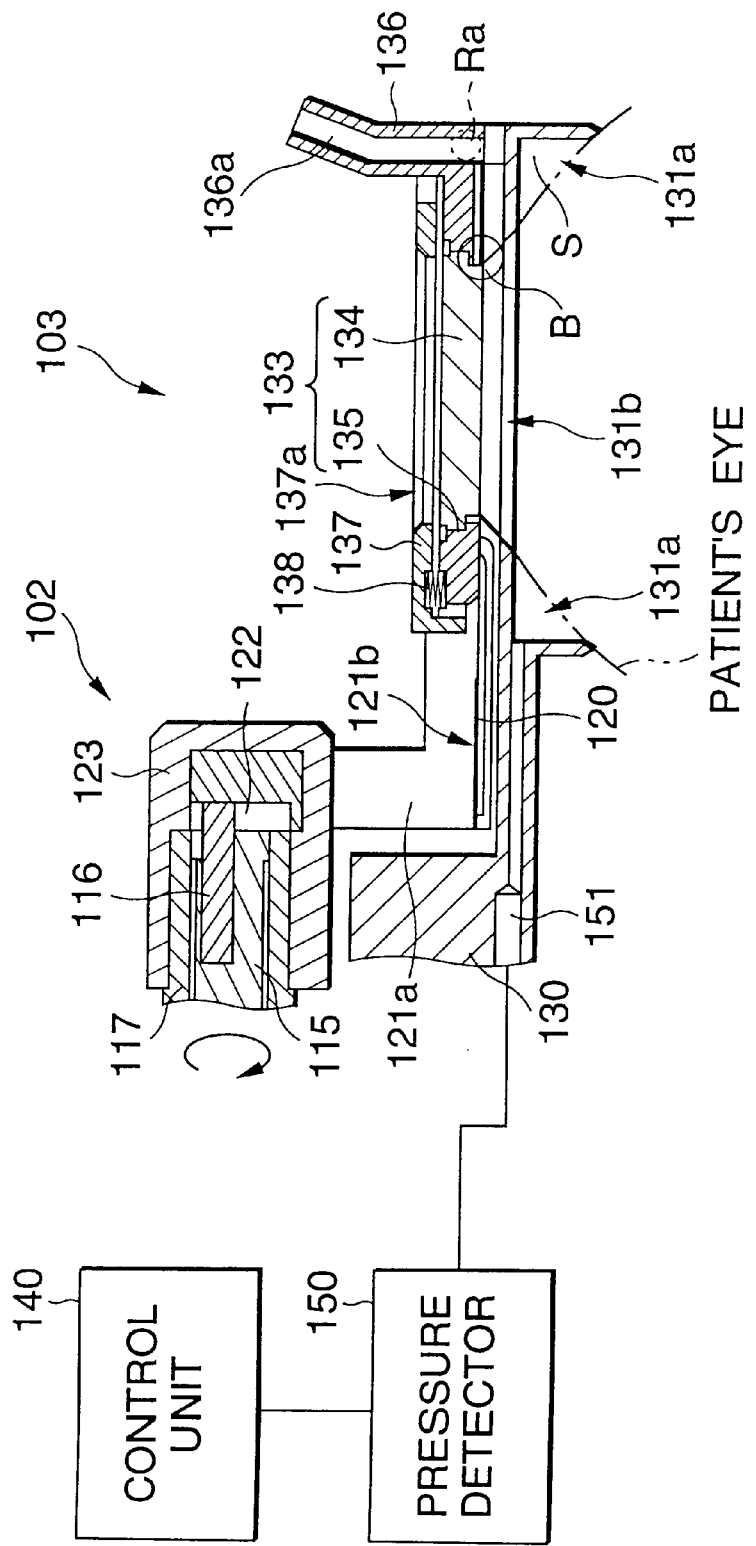
FIG. 9 is an enlarged explanatory diagram of the cutting unit and the suction unit.

Furthermore, as shown in FIG. 9, a pressure detector 150 as described in connection with the first embodiment is connected to the recessed portion 131a through an unillustrated tube and a suction passage 151 formed in the base 130, so as to detect the air pressure in the space S. The control unit 140 controls the driving of the motors 111 and 112 on the basis of the air pressure detected by the detector 150, as described above. This arrangement makes the surgery more efficient and accurate.

After the edge of the blade 120 has thus effected incision with the hinge portion left to complete the formation of the flap, the air is introduced into the space S and the gap Sc to release the suction, and the apparatus is removed. Subsequently, a refractive correction amount of the corneal stroma is ablated and removed using laser light, and the flap is returned to its original position, thereby completing the surgery.

Although in the above-described embodiments, a metallic blade formed of stainless steel, steel, or the like is used as the blade, and the incision of the cornea is effected by oscillating the blade, it is also possible to use a mineral blade having a blade edge of a mineral such as diamond or sapphire. If a sufficiently sharp mineral blade is used, the incision may be carried out without laterally oscillating the blade in addition, to reduce the frictional force with respect to the flap, it is effective to provide porous portions or fine irregularities on the upper surface portion of the blade which comes into contact with the flap formed by incision, or to form the upper surface portion into a honeycomb shape so that the contact area of that portion with the flap is reduced.

As the mechanism of feeding the blade, a description has been made on the type which incises the corneal epithelium by rectilinearly moving the blade in the incising direction. It is also possible to adopt a mechanism in which the corneal epithelium is incised by rotatively moving the blade. As for the mechanism for rotatively moving the blade, reference is made to copending U.S. application Ser. No. 09/108,966 (Japanese Patent Unexamined Publication No. Hei. 11-19115).

Both the feeding of the blade and the lateral oscillation of the blade may be effected by a single motor, or only the lateral oscillation of the blade may be effected by a motor, whereas the feeding of the blade may be effected manually using a rotating gear or the like. In the latter case, only the control of the lateral oscillation of the blade is effected on the basis of the detected air pressure.

Further, in order to impart lateral oscillations to the blade (in order to rotate the rotating shaft), an air turbine or the like may be applied in stead of the motor.

As described above, in accordance with the present invention, it is possible to form a satisfactory flap easily.

What is claimed is:

1. A corneal surgical apparatus for incising a cornea of a patient's eye in a layered form, comprising;
    fixing means adapted to abut against the patient's eye, said fixing means having an opening from which the cornea is projected;
    first sucking means for sucking air in a gap formed between said fixing means and the patient's eye, so as to fix said fixing means to the patient's eye;
    a blade for incising the cornea projected from the opening;
    oscillating means for laterally oscillating said blade;
    blade moving means for rectilinearly moving said blade in an incising direction;
    applanating means for applanating the cornea, said applanating means including a flat plate defining a flat side opposing the cornea, and second sucking means for sucking air in a gap between said flat plate and the cornea;
    plate moving means for moving said flat plate in a direction away from a surface of said blade in conjunction with the rectilinear movement of said blade by said blade moving means;
    pressure detecting means for detecting air pressure in the gap which changes due to the suction by said first sucking means; and
    drive controlling means for controlling at least one of said oscillating means and said blade moving means on the basis of information on the pressure detected by said pressure detecting means.

2. The corneal surgical apparatus according to claim 1, wherein said plate moving means includes:
    rotating means for rotating said flat plate in a vertical direction about a shaft provided at one end of said fixing means; and
    a projection provided above said blade to upwardly push said flat plate without interposing the incised cornea between said projection and said flat plate.

3. The corneal surgical apparatus according to claim 1, further comprising:
    suction controlling means for controlling said first sucking means on the basis of the information on the pressure detected by said pressure detecting means.

4. A corneal surgical apparatus for incising the cornea of a patient's eye in a layered form, comprising:
    fixing means adapted to abut against the patient's eye, said fixing means having an opening from which the cornea is projected;
    sucking means for sucking air in a gap formed between said fixing means and the patient's eye so as to fix said fixing means to the patient's eye;
    a blade for incising the cornea projected from the opening;
    driving means far driving said blade;
    pressure detecting means for detecting air pressure in the gap which changes due to the suction by said sucking means; and
    drive controlling means for controlling said driving means on the basis of information on the pressure detected by said pressure detecting means.

5. The corneal surgical apparatus according to claim 4, wherein said driving means includes oscillating means for laterally oscillating said blade and moving means for rectilinearly or rotatively moving said blade in an incising direction, and said drive controlling means controls at least one of said oscillating means and said moving means on the basis of the information on the pressure detected by said pressure detecting means.

6. The corneal surgical apparatus according to claim 5, wherein said drive controlling means linearly adjusts at least one of the number of oscillations of said oscillating means and a moving velocity of said moving means on the basis of the air pressure detected by said pressure detecting means.

7. The corneal surgical apparatus according to claim 5, wherein said drive controlling means determines which one of a plurality of stages the air pressure detected by said pressure detecting means belongs to, and adjusts at least one of the number of oscillations of said oscillating means and a moving velocity of said moving means on the basis of the stage thus determined.

8. The corneal surgical apparatus according to claim 5, wherein said moving means includes means for rectilinearly moving said blade, and said apparatus further comprising:

applanating means for applanating the cornea, said applanating means including a flat plate defining a flat side opposing the cornea and second sucking means for sucking air in a gap between said flat plate and the cornea; and second moving means for moving said flat plate in a direction away from a surface of said blade in conjunction with the rectilinear movement of said blade by said moving means.

9. The corneal surgical apparatus according to claim 8, wherein said second moving means includes:

rotating means for rotating said flat plate in a vertical direction about a shaft provided at one end of the fixing means; and a projection provided above said blade to upwardly push said flat plate without interposing the incised cornea between said projection and said flat plate.

10. The corneal surgical apparatus according to claim 4, further comprising:

upper-limit setting means for setting a value of an upper limit for the detected air pressure, wherein said drive controlling means stops the operation of said driving means when the value of the air pressure detected by said pressure detecting means is more positive than the value of the upper limit.

11. The corneal surgical apparatus according to claim 8, further comprising:

alarm means for notifying an operator of a fact that the value of the air pressure detected by said pressure detecting means is more negative than the value of the upper limit.

12. The corneal surgical apparatus according to claim 10, further comprising:

lower-limit setting means for setting a value of a lower limit for the detected air pressure, wherein said drive controlling means stops the operation of said driving means when the value of the air pressure detected by said pressure detecting means is more negative than the value of the upper limit.

13. The corneal surgical apparatus according to claim 4, further comprising:

lower-limit setting means for setting a value of a lower limit for the detected air pressure, wherein said drive controlling means stops the operation of said driving means when the value of the air pressure detected by said pressure detecting means is more negative than the value of the lower limit.

14. The corneal surgical apparatus according to claim 4, further comprising:

upper-limit setting means for setting a value of an upper limit for the detected air pressure, wherein said drive controlling means starts the operation of said driving means when the value of the air pressure detected by said pressure detecting means is more negative than the value of the upper limit.

15. The corneal surgical apparatus according to claim 4, further comprising:

suction controlling means for controlling said sucking means on the basis of the information on the pressure detected by said pressure detecting means.

16. A corneal surgical apparatus for incising the cornea of a patient's eye in a layered form, comprising:

fixing means adapted to abut against the patient's eye, said fixing means having an opening from which the cornea is projected;

a blade for incising the cornea projected from the opening;

blade moving means for rectilinearly moving said blade in an incising direction;

applanating means for applanating the cornea, said applanating means including a flat plate defining a flat side opposing the cornea and second sucking means for sucking air in a gap between said flat plate and the cornea; and plate moving means for moving said flat plate in a direction away from a surface of said blade in conjunction with the rectilinear movement of said blade by said blade moving means.

17. The corneal surgical apparatus according to claim 16, wherein said plate moving means has rotating means for rotating said flat plate in a vertical direction about a shaft provided at one end of said fixing means.

18. The corneal surgical apparatus according to claim 16, wherein said plate moving means includes:

rotating means for rotating said flat plate in a vertical direction about a shaft provided at one end of said fixing means; and a projection provided above said blade to upwardly push said flat plate without interposing the incised cornea between said projection and said flat plate.

19. The corneal surgical apparatus according to claim 16, wherein said blade has frictional-force reducing means for reducing a frictional force acting on the cornea cut in the layered form.

20. The corneal surgical apparatus according to claim 19, wherein said frictional-force reducing means includes a frictional-force reducing coating applied on a surface of said blade which comes into contact with the cornea cut in the layered form.

21. The corneal surgical apparatus according to claim 16, further comprising:

urging means for urging said flat plate toward a surface of said blade.

22. The corneal surgical apparatus according to claim 16, further comprising:

oscillating means for laterally oscillating said blade.

\* \* \* \* \*

UNITED STATES PATENT AND TRADEMARK OFFICE
CERTIFICATE OF CORRECTION

PATENT NO. : 6,059,805
DATED : May 9, 2000
INVENTOR(S) : Masahiro SUGIMURA et al.

It is certified that error appears in the above-identified patent and that said Letters Patent is hereby corrected as shown below:

Title Page, Item [73], in the Assignee, "Gamagori-shi" should read --Gamagori--.

Claim 1, col. 13, line 55, "comprising;" should read --comprising:--.

Claim 4, col. 14, line 41, "far driving" should read --for driving--.

Claim 11, col. 15, line 30, "claim 8" should read --claim 10--.

Signed and Sealed this

Tenth Day of April, 2001

Attest:

NICHOLAS P. GODICI

*Attesting Officer*   *Acting Director of the United States Patent and Trademark Office*